(12) United States Patent
Jenkins (10) Patent No.: US 7,794,940 B2
(45) Date of Patent: Sep. 14, 2010

(54) DETECTING T(1;19)

(75) Inventor: Robert B. Jenkins, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 557 days.

(21) Appl. No.: 11/744,647

(22) Filed: May 4, 2007

(65) Prior Publication Data

US 2007/0259369 A1 Nov. 8, 2007

Related U.S. Application Data

(60) Provisional application No. 60/798,376, filed on May 5, 2006.

(51) Int. Cl.
C12Q 1/68 (2006.01)
(52) U.S. Cl. ......................................................... 435/6
(58) Field of Classification Search ........................ None
See application file for complete search history.

(56) References Cited

U.S. PATENT DOCUMENTS

2009/0215055 A1  8/2009 French et al.

FOREIGN PATENT DOCUMENTS

WO  WO 2007/069882 A1  6/2007

OTHER PUBLICATIONS

Uckun et al. Journal of Clinical Oncology, vol. 16, No. 2 (Feb. 1998): pp. 527-535.*
Parmiter et al. Cancer Research 46, 1526-1529, Mar. 1986.*
Baldini et al., "A Human Alphoid DNA Clone from the EcoRI Dimeric Family; Genomic and Internal Organization and Chromosomal Assignment," *Genomics*, 1989, 5(4):822-828.
Buckner et al., "Phase II Trial of Procarbazine, Lomustine, and Vincristine as Initial Therapy for Patients with Low-Grade Oligodendroglioma or Oligastrocytoma: Efficacy and Associations with Chromosomal Abnormalities," *J. Clin. Onco.*, 2002, 21(2):251-255.

Korhonen et al., "Tumor Suppressor Gene BRCA-1 Is Expressed by Embryonic and Adult Neural Stem Cells and Involved in Cell Proliferation," *J. Neurosci. Res.*, 2003, 71(6):769-776.
Magnani et al., "A recurrent 19q11-12 Breakpoint Suggested by Cytogenetic and Fluorescence in Situ Hybridization Analysis of Three Glioblastoma Cell Lines," *Cancer Genet. Cytogenet.*, 1999, 110:82-86.
Shaw et al., "Prospective Randomized Trial of Low-Versus High-Dose Radiation Therapy in Adults with Supratentorial Low- Grade Glioma: Initial Report of a North Central Cancer Treatment Group/Radiation Tehrapy Oncology Group/Eastern Cooperative Oncology Group Study," *J. Clin. Oncol.*, 2002, 20(9):2267-2276.
Smith et al., "Alterations of Chromosome Arms 1p and 19q as Predictors of Survival in Oligodendrogliomas, Astrocytomas, and Mixed Oligoastrocytomas," J. Clin. Oncol., 2000, 18(3):636-645.
GenBank Accession No. AQ138163, dated Sep. 24, 1998, 2 pgs.
GenBank Accession No. AQ141904, dated Sep. 24, 1998, 2 pgs.
GenBank Accession No. AQ186177, dated Nov. 1, 1998, 2 pgs.
GenBank Accession No. AQ212877, dated Sep. 18, 1999, 2 pgs.
GenBank Accession No. AQ338123, dated Mar. 6, 1999, 2 pgs.
GenBank Accession No. AQ338370, dated Mar. 6, 1999, 2 pgs.
GenBank Accession No. AQ434272, dated Mar. 31, 1999, 2 pgs.
GenBank Accession No. AQ461333, dated Apr. 23, 1999, 2 pgs.
GenBank Accession No. AQ464301, dated Apr. 23, 1999, 2 pgs.
GenBank Accession No. AQ495017, dated Apr. 28, 1999, 2 pgs.
GenBank Accession No. AQ633079, dated Jun. 17, 1999, 2 pgs.
GenBank Accession No. AQ633080, dated Jun. 17, 1999, 2 pgs.
Griffin, Constance A et al., "Identification of der(1;19)(q10;p10) in Five Oligodendrogliomas Suggests Mechanism of Concurrent 1p and 19q Loss," *J. Neuropathol. Exp. Neurol.*, vol. 65(10):988-994 (2006).
Jenkins, Robert B. et al., "A t(1;19)(q10;p10) Mediates the Combined Deletions of 1p and 19q and Predicts a Better Prognosis of Patients with Oligodendroglioma," *Cancer Res.*, 66(20):9852-9861 (2006).
Jenkins, Robert B., et al., "A t(1;19)(q10;p10) mediates the combined deletions of 1p and 19q in human oligodendrogliomas," Proc. Amer. Assoc. Cancer Res., Abstract #5730, vol. 47 (2006).

\* cited by examiner

*Primary Examiner*—Juliet C Switzer
(74) *Attorney, Agent, or Firm*—Fish & Richardson P.C.

(57) ABSTRACT

This document provides methods and materials related to detecting t(1;19) as well as methods and materials for identifying or assessing cancer within a mammal (e.g., a human). For example, methods for assessing the aggressiveness of a low-grade glioma in a human are provided.

16 Claims, 4 Drawing Sheets

DETECTING T(1;19)

CROSS-REFERENCE TO RELATED APPLICATIONS

This application claims the benefit of U.S. Provisional Application Ser. No. 60/798,376, filed on May 5, 2006.

STATEMENT AS TO FEDERALLY SPONSORED RESEARCH

This invention was made with government support under grant CA85799 awarded by the National Institutes of Health's National Cancer Institute. The government has certain rights in the invention.

BACKGROUND

1. Technical Field

This document relates to methods and materials involved in detecting chromosome translocations. For example, this document provides methods and materials for detecting t(1;19)(q10;p10).

2. Background Information

The nervous system generally has two types of cells, neurons and neuroglia. Neuroglia, also known as glial cells, often surround the neuron and can provide a supportive role by nourishing, protecting, and supporting neurons. Brain tumor that develop from glial cells are called gliomas. Gliomas can be divided into subgroups depending on the origin of the glial cells. For example, astrocytomas, oligodendrogliomas, and mixed oligoastrocytomas are types of gliomas.

SUMMARY

This document provides methods and materials relating to identifying or assessing cancer (e.g., low grade gliomas) in a mammal (e.g., a human). For example, this document provides methods and materials that can be used to determine whether or not a mammal contains cells having a t(1;19) such as a t(1;19)(q10;p10). The presence of cells having a t(1;19) (q10;p10) can indicate that a mammal has cancer (e.g., a glioma such as an oligodendroglioma). Identifying mammals (e.g., humans) having cancer can allow clinicians and patients to select appropriate treatment options. This document also provides methods and materials that can be used to determine whether or not cancer cells (e.g., low grade glioma cells) from a mammal contain a t(1;19) such as a t(1;19)(q10;p10). The presence of cancer cells having a t(1;19) can indicate that the mammal has a less aggressive cancer, that the mammal has a better prognosis, or that the mammal has a higher likelihood of responding to treatment (e.g., radiation treatment, chemotherapy, surgery, or a combination thereof) than a mammal having a comparable cancer lacking a t(1;19).

This document also provided kits containing a probe set having two or more probes that are at least 10,000 nucleotides in length (e.g., at least 20,000 nucleotides in length; at least 50,000 nucleotides in length; at least 75,000 nucleotides in length; at least 100,000 nucleotides in length; or at least 150,000 nucleotides in length) and have the ability to hybridize to a sequence from chromosome 19 and not chromosome 1 or chromosome 5. Such probes can be BAC clones designated as RP11-771C12, RP11-587H3, RP11-460G17, CTD-3173A10, CTD-3074B13, or RP11-677G1. The kits provided herein can contain one or more probes having the ability to hybridize to a sequence from chromosome 1 and not chromosome 5 or chromosome 19. Such probes can be a CEP1 probe or a CEN1 probe. Such kits can be used to detect a t(1;19) such as t(1;19)(q10;p10).

In general, one aspect of this document features a method of determining the prognosis of a mammal having cancer. The method comprising, or consists essentially of, determining whether or not a cancer cell from the mammal contains a t(1;19), wherein the presence of the t(1;19) in the cancer cell indicates that the mammal has cancer that is less aggressive than aggressive cancer cells lacking the t(1;19). The mammal can be a human. The cancer can be an oligodendroglioma. The cancer can be a mixed oligoastrocytoma. The t(1;19) can be a t(1;19)(q10;p10). The determining step can comprise fluorescent in situ hybridization. The determining step can comprise fluorescent in situ hybridization with a CEP1 probe. The determining step can comprise fluorescent in situ hybridization with a 19p12 probe set.

In another aspect, this document features a method of determining risk of cancer progression in a mammal with cancer. The method comprises, or consists essentially of, determining whether or nor a cancer cell from the mammal contains a t(1;19), wherein the presence of the t(1;19) in the cancer cell indicates that the mammal has an increased progression-free survival as compared to a mammal having aggressive cancer cells lacking the t(1;19). The mammal can be a human. The cancer can be an oligodendroglioma. The cancer can be a mixed oligoastrocytoma. The t(1;19) can be a t(1;19)(q10;p10). The determining step can comprise fluorescent in situ hybridization. The determining step can comprise fluorescent in situ hybridization with a CEP1 probe. The determining step can comprise fluorescent in situ hybridization with a 19p12 probe set.

In another aspect, this document features an article of manufacture comprising, or consisting essentially of, a container comprising, or consisting essentially of, a probe having the ability to hybridize to human chromosome 1 sequences and a probe set comprising, or consisting essentially of, probes having the ability to hybridize to human chromosome 19 sequences, wherein the probe and the probe set have the ability to detect a t(1;19). The probe can comprise, or consisting essentially of, a CEP1 probe. The probe set can comprise, or consisting essentially of, a 19p12 probe set. The probe can comprise a fluorescent label. The probes of the probe set can comprise a different fluorescent label.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 contains micrographs of karyotype and fluorescent in situ hybridization results identifying a t(1;19)(q10;p10). A) Karyotype of an oligodendroglioma tumor. The arrow indicates the t(1;19)(q10;p10). B) G-banded metaphase. The arrow indicates the t(1;19)(q10;p10). C) Metaphase FISH using whole chromosome painting probes. The arrow indicates the t(1;19). Spectrum Green=1 WCP; Spectrum Orange=19 WCP. D) Metaphase FISH using CEP1 labeled with Spectrum Orange and a BAC probe set for 19p12 labeled with Spectrum Green. The arrow indicates fusion of the probes at the translocation site. E) Interphase FISH using CEP1 labeled with Spectrum Orange and a BAC probe set for 19p12 labeled with Spectrum Green. The arrow indicates fusion signal.

DETAILED DESCRIPTION

This document provides methods and materials relating to identifying or assessing cancer (e.g., low grade gliomas) in a mammal (e.g., a human). For example, this document provides methods and materials that can be used to determine whether or not a mammal contains cells having a t(1;19) such as a t(1;19)(q10;p10). Any method can be used to assess a mammal for the presence or absence of cells having a t(1;19). For example, the FISH assays provided herein can be used to determine whether or not a mammal contains cells having a t(1;19). Other methods that can be used include, without limitation, PCR and end-sequence profiling. If a mammal is determined to contain cells having a t(1;19), then that mammal can be classified as having cancer (e.g., as having a glioma such as an oligodendroglioma). The mammal also can be classified as have a less aggressive form of cancer based on the presence of cells having a t(1;19). In some cases, the mammal can be instructed to undergo cancer treatments such as radiation therapy, chemotherapy, surgery, or a combination thereof. If a mammal is determined not to contain cells having a t(1;19), then that mammal can be classified either as not having cancer or as having an aggressive form of cancer (e.g., as having an aggressive glioma such as an anaplastic oligodendroglioma). In some cases, such a mammal can be instructed to undergo aggressive cancer treatments such as radiation therapy, chemotherapy, surgery, or a combination thereof.

This document also provides methods and materials that can be used to determine whether or not cancer cells (e.g., low grade glioma cells) from a mammal contain a t(1;19) such as a t(1;19)(q10;p10). A low grade glioma can be a WHO grade I glioma or a WHO grade II glioma. If a mammal is determined to contain cancer cells (e.g., oligodendroglioma cells) having a t(1;19), then that mammal can be classified as having a less aggressive form of cancer (e.g., a less aggressive form of oligodendroglioma). In some cases, the mammal can be classified as having a prognosis that is better than a corresponding patient having cancer cells lacking the t(1;19). In some cases, the mammal can be classified as having a high likelihood of responding to an anti-cancer treatment (e.g., radiation treatment, chemotherapy, surgery, or a combination thereof). If a mammal is determined to contain cancer cells lacking a t(1;19), then that mammal can be classified having an aggressive form of cancer (e.g., an anaplastic oligodendroglioma). In some cases, the mammal can be classified as having a prognosis that is poorer than a corresponding patient having cancer cells with the t(1;19). In some cases, the mammal can be classified as having a low likelihood of responding to an anti-cancer treatment (e.g., radiation treatment, chemotherapy, surgery, or a combination thereof).

Any type of sample can to obtained and assessed for a t(1;19). For example, tissue biopsies from a tumor can be used. In some cases, paraffin embedded glioma sample can be used to determine whether or not a mammal contains cancer cells having a t(1;19). The paraffin embedded glioma sample can be a formalin-fixed, paraffin embedded glioma sample.

In one embodiment, this document provides a collection of nucleic acid molecules (e.g., probes) having the ability to detect rearrangements of chromosomes 1 and 19. in some cases, a collection of nucleic acid molecules provided herein can have the ability to hybridize to chromosome 1 nucleic acid sequences or chromosome 19 nucleic acid sequences or both chromosome 1 nucleic acid sequences and chromosome 19 nucleic acid sequences. For example, each probe within a collection can have the ability to hybridize to a chromosome 1 sequence. In some cases, a collection can contain at least one (e.g., 2, 3, 4, 5, 10, or more) nucleic acid molecule having the ability to hybridize to a chromosome 1 nucleic acid sequence and at least one (e.g., 2, 3, 4, 5, 10, or more) nucleic acid molecule having the ability to hybridize to a chromosome 19 sequence. For example, a collection of isolated nucleic acid molecules provided herein can contain a probe set having probes with the ability to hybridize to a chromosome 1 nucleic acid sequence and a probe set having probes with the ability to hybridize to a chromosome 19 nucleic acid sequence (e.g., a 19p12 probe set). Examples of probes having the ability to hybridize to a chromosome 1 nucleic acid sequence include, without limitation, CEP1 and CEN1. Collections of isolated nucleic acid molecules having the ability to detect t(1;19) can include a vector such as a bacterial artificial chromosome (BAC) or a fosmid. For example, a collection of nucleic acid molecules provided herein can be a collection of BACs containing nucleic acid sequences capable of hybridizing to a chromosome 1 nucleic acid sequence or a chromosome 19 nucleic acid sequence.

The isolated nucleic acid molecule provided herein can have any length. In some cases, isolated nucleic acid molecules provided herein (e.g., nucleic acid molecules having the ability to detect rearrangements of chromosomes 1 and 19) can be more than 50 bp in length (e.g., more than 100 bp, 250 bp, 500 bp, 1 kb, 2 kb, 5 kb, 7 kb, 10 kb, 20 kb, 50 kb, 100 kb, or 300 kb in length). An isolated nucleic acid molecule of a probe set provided herein can have a sequence that overlaps with another member of the probe set. In some cases, each nucleic acid molecule of a probe set can have a sequence that is distinct from the sequences of the other members of the probe set.

Isolated nucleic acid molecules of the collections provided herein can hybridize to chromosome 1 or chromosome 19 nucleic acid sequences present in either an intron or an exon. Introns and exons to which isolated nucleic acid molecules having the ability to detect rearrangements of chromosomes 1 and 19 can hybridize can be nucleic acid sequences of the q or p arms of either chromosome 1 or 19. For example, collections of isolated nucleic acid molecules having the ability to detect a rearrangement of chromosomes 1 and 19 can hybridize to sequences of the p arm of chromosome 19 (e.g., 19p12). In some cases, collections of isolated nucleic acid molecules having the ability to detect rearrangements of chromosomes 1 and 19 can hybridize to alpha satellite regions (e.g., a chromosome enumeration probe (CEP)).

The term "nucleic acid" as used herein can be RNA or DNA, including cDNA, genomic DNA, and synthetic (e.g. chemically synthesized) DNA. The nucleic acid can be double-stranded or single-stranded. Where single-stranded, the nucleic acid can be the sense strand or the antisense strand. In addition, nucleic acid can be circular or linear.

The term "isolated nucleic acid" as used herein includes any non-naturally-occurring nucleic acid sequence since such non-naturally-occurring sequences are not found in nature and do not have immediately contiguous sequences in a naturally-occurring genome. An isolated nucleic acid can be, for example, a DNA molecule, provided one of the nucleic acid sequences normally found immediately flanking that DNA molecule in a naturally-occurring genome is removed or absent.

One or more of the isolated nucleic acid molecules provided herein can be labeled (e.g., fluorescently or radioactively labeled) and used as probes (e.g., fluorescent in situ hybridization (FISH) probes). In some cases, the collections of isolated nucleic acid molecules provided herein can be dual fusion FISH probe sets (e.g., D-FISH probe sets) that can be used to identify chromosome rearrangement products (e.g., der(1;19)(q10;p10)). Typically, a D-FISH probe set can have (1) at least one probe that is labeled with a fluorophore (e.g., SpectrumGreen™ or SpectrumOrange™) and that has the ability to hybridize to a nucleic acid sequence of one chromosome, and (2) at least another probe that is labeled with a different fluorophore and that has the ability to hybridize to a nucleic acid sequence of a second chromosome. It will be appreciated that the fluorophores used herein can be substituted with alternative sets of distinguishable fluorophores.

The methods and materials provided herein can be used to predict the clinical outcome of a patient with a cancer having a rearrangement of chromosomes 1 and 19 (e.g., oligodendroglioma and oligoastrocytoma). In some cases, the materials and methods provided herein can be used for predicting the response of a patient with a cancer to therapy (e.g., chemotherapy, radiation therapy, surgery, or combinations thereof). For example, a patient with a cancer containing a t(1;19) can have increased survival time when treated with radiation therapy plus chemotherapy as compared to a similarly-treated patient with a cancer lacking a t(1;19). In some cases, the materials and methods provided herein can be used for predicting the overall survival time of a patient having a cancer. For example, a patient with a cancer containing a t(1;19) can have increased survival time as compared to a patient with a cancer lacking a t(1.19). In some cases, the methods provided herein can include determining the presence or absence of a t(1;19) in a tissue sample from a mammal (e.g., a human) and correlating the t(1;19) status with prognosis or risk of cancer progression (e.g., time of overall survival, likelihood of five-year survival, time of progression-free survival, or likelihood of five-year progression-free survival). Any type of tissue sample can be used. For example, a tissue sample obtained from a tumor (e.g., a resection or biopsy of a tumor) can be used.

The invention will be further described in the following examples, which do not limit the scope of the invention described in the claims.

EXAMPLES

Example 1

Methods and Materials

Patients:

Initial studies used material from 21 patients enrolled in a Mayo Clinic Neuro-Oncology project entitled "Molecular Markers of Glioma Initiation and Progression." Additional clinical validation used 125 patients enrolled on NCCTG trial 94-72-53 "Diagnostic and Prognostic Markers in Low-Grade Gliomas." NCCTG 94-72-53 is a correlative translational biomarker study of the North Central Cancer Treatment Group. Eligible patients were those enrolled in two prospective NCCTG trials for newly-diagnosed low-grade glioma: 86-72-51, a phase III trial of 50.4Gy versus 64.8Gy RT (Shaw et al., *J. Clin. Oncol.*, 20(9):2267-76 (2002)), and 93-72-02, a phase II trial of 6 cycles of PCV (procabazine, 1-(2-chloroethyl)-3-cyclohexyl-1-nitrosourea, and Vincristine) chemotherapy followed by 54.0Gy RT (Buckner et al., *J. Clin. Onco.*, 21(2):251-5 (2002)). Paraffin-embedded tumor tissue was available and obtained for 98 patients from these two trials. Table 1 describes the clinical and pathologic features of the patients enrolled on 94-72-53 for whom paraffin tissue was available. Two patients had WHO grade I gliomas, the remaining 96 gliomas were WHO grade II. Pilocytic astrocytomas were not included.

TABLE 1

Clinical and histologic characteristics of low-grade glioma patients eligible for NCCTG 94-72-53.

| Variable | All Eligible Patients (n = 125) | Deletion Successful Patients (n = 91) | p-value* | Fusion Successful Patients (n = 84) | p-value** |
|---|---|---|---|---|---|
| Age in years, |  |  | 0.46 |  | 0.27 |
| Median (range) | 39 (18-72) | 38 (18-72) |  | 38 (18-72) |  |
| Gender, N(%) |  |  | 0.92 |  | 0.92 |
| Male | 75 (60%) | 54 (59%) |  | 51 (60%) |  |
| Female | 50 (40%) | 37 (41%) |  | 33 (40%) |  |
| MMSE score (out of 30), |  |  | 0.83 |  | 0.94 |
| Median (range) | 29 (21-30) | 30 (21-30) |  | 29 (21-30) |  |
| Performance Score, N (%) |  |  | 0.86 |  | 0.56 |
| 0 | 42 (34%) | 29 (32%) |  | 29 (35%) |  |
| 1 | 14 (11%) | 9 (10%) |  | 10 (12%) |  |

TABLE 1-continued

Clinical and histologic characteristics of low-grade glioma patients eligible for NCCTG 94-72-53.

| | All Eligible Patients (n = 125) | | Deletion Successful Patients (n = 91) | | p-value* | Fusion Successful Patients (n = 84) | | p-value** |
|---|---|---|---|---|---|---|---|---|
| 2 | 3 | (2%) | 1 | (1%) | | 0 | (0%) | |
| Missing | 66 | (53%) | 52 | (57%) | | 45 | (53%) | |
| Trial/Treatment, N (%) | | | | | 0.76 | | | 0.87 |
| 867251/64.8Gy | 43 | (34%) | 30 | (33%) | | 27 | (32%) | |
| 867251/50.4Gy | 46 | (37%) | 38 | (42%) | | 34 | (41%) | |
| 937202/PCV + 50.4Gy | 34 | (27%) | 22 | (24%) | | 22 | (26%) | |
| 867251/observation | 2 | (2%) | 1 | (1%) | | 1 | (1%) | |
| Histologic Type, N (%) | | | | | 0.38 | | | 0.41 |
| Oligodendroglioma | 57 | (45%) | 47 | (52%) | | 42 | (50%) | |
| Mixed Oligoastrocytoma | 41 | (33%) | 31 | (34%) | | 30 | (36%) | |
| Astrocytoma | 27 | (22%) | 13 | (14%) | | 12 | (14%) | |

*p-value comparing deletion successful patients with all eligible patients
**p-value comparing fusion successful patients with all eligible patients Culture:

A fresh oligodendroglioma sample was dissociated in collagenase. Cells were rinsed in 10% FBS/MEM media and cultured in Human Neuroproliferative Media (StemCell Technologies, Vancouver, BC, Canada) at 37° C. in a gassed incubator (5% $CO_2$, 5% $O_2$) using methods for culturing neural stem cells described elsewhere (Korhonen et al., *J. Neurosci. Res.*, 71(6):769-76 (2003)). Tumor cells grew as suspended clumps and were harvested and fixed using standard cytogenetic techniques. Metaphase spreads were obtained and G-banded using standard cytogenetic techniques. The International System for Cytogenetic—Nomenclature (ISCN) was used to describe the cytogenetic anomaly (ISCN (2005):Guidelines for Cancer Cytogenetics. A supplement to an International System for Human Cytogenetic Nomenclature. L. G. Shaffer, N. Tommerup, eds, S. Karger, New York. 15).

FISH

FISH analyses of fixed cytogenetic preparations from the fresh oligodendroglioma were performed using standard methods.

1p and 19q deletion analysis of formalin-fixed paraffin embedded gliomas by FISH was performed as described elsewhere (Smith et al., *J. Clin. Oncol.*, 18(3):636-45 (2000)).

The prehybridization, hybridization, and post hybridization procedures for the t(1;19) translocation analysis of formalin-fixed paraffin-embedded tissues were similar to methods described elsewhere (Smith et al., *J. Clin. Oncol.*, 18(3): 636-45 (2000)).

For 1p and 19q deletion analysis of metaphase and interphase nuclei (for both fresh and paraffin-embedded tumor specimens), nick-translated bacterial artificial chromosome (BAC) contig probes for the target region 1p36 (Spectrum Orange-Vysis) with a control region at 1 q24 (Spectrum Green-Vysis) and the control region 19p 13 (Spectrum Green) with the target region 19q 13 (Spectrum Orange) were used as described elsewhere (Smith et al., *J. Clin. Oncol.*, 18(3):636-45 (2000)). Whole chromosome painting probes (WCP-Vysis) for 1 and 19 were used in the analysis of metaphase spreads from the primary tumor. For the t(1;19) translocation analysis (e.g., a fusion analysis), a chromosome 1 alpha satellite probe, CEP1, in Spectrum Orange (Vysis) was co-hybridized with a BAC contig probe set for 19p 12 that was nick-translated and labeled in Spectrum Green. The BAC clones included in the 19p12 probe set were: RP11-771C12, RP11-587H3, RP11-460G17, CTD-3173A10, CTD-3074B13 and RP11-677G1. All BAC clones were supplied by Invitrogen (Carlsbad Calif.), and sequence information for the BAC clones are provided in Table 2.

TABLE 2

BAC clone information.

| | | Start Sequence data | | End Sequence Data | |
|---|---|---|---|---|---|
| Start Position | End Position | Accession Number | Nucleotide Positions | Accession Number | Nucleotide Positions |
| BAC ID = RP11-771C12 | | | | | |
| 24061052 | 24209607 | AQ495017 | 24061052-24061426 | AQ461333 | 24209110-24209607 |
| BAC ID = RP11-587H3 | | | | | |
| 24107631 | 24298603 | AQ338370 | 24107631-24108070 | AQ338123 | 24298187-24298603 |
| BAC ID = RP11-460G17 | | | | | |
| 23846152 | 24003299 | AQ633079 | 23846152-23846688 | AQ633080 | 24002803-24003299 |

TABLE 2-continued

BAC clone information.

| Start Position | End Position | Start Sequence data | | End Sequence Data | |
|---|---|---|---|---|---|
| | | Accession Number | Nucleotide Positions | Accession Number | Nucleotide Positions |
| BAC ID = CTD-3173A10 | | | | | |
| 23942396 | 24153371 | AQ212877 | 23942396-23942789 | AQ141904 | 24152993-24153371 |
| BAC ID = CTD-3074B13 | | | | | |
| 23529940 | 23691698 | AQ186177 | 23529940-23530369 | AQ138163 | 23691334-23691698 |
| BAC ID = RP11-677G1 | | | | | |
| 23709849 | 23871468 | AQ434272 | 23709849-23710295 | AQ464301 | 23870981-23871468 |

Scoring Criteria:

For the deletion portion of the study, 100 nuclei were scored per specimen for number of red and green signals per nuclei. Specimen were considered deleted if the red/green ratio was less than 0.85, and aneusomy if there were greater than 30% of the nuclei with 3 green signals.

For the translocation portion of the study, the scoring criteria for fusion required that the red and green signals be within two signal widths of each other. This less strict fusion requirement was due to the potential 4.0-6.5 Mb gap between the probes when the hypothesized translocation was present. The range in estimated gap size is based on the distance from the position of BAC RP11-587H3 (the 19p BAC closest to the centromere that did not show cross-hybridization) to the center and q-arm end of the chromosome19 centromere (UCSC Genome Browser on Human May 2004 Assembly Chromosome 19p12-q12: at http for "genome.ucsc.edu/cgi-bin/hgTracks" and at http for "genome.ucsc.edu/cgi-bin/hgc?hgsid=67301676&o=26700000&t=28500000&g=cytoBand&i=p11&c=chr19&1=24107630&r=32298603&db=hg17&pix=620"). Fifty nuclei were scored by each of two independent scorers. Diploid nuclei were classified as abnormal if one or more fusion signals were identified. Aneuploid nuclei were classified as abnormal if apparently triploid cells had one or more fusion signals and apparently tetraploid cells had two or more fusion signals. The criteria for translocation was established by scoring 12 normal glial specimens and five abnormal astrocytoma and GBM specimens known not to contain combined 1p and 19q deletion. For a case to be classified as containing the t(1;19), 60% or greater of the nuclei were required to have fusion of the red and green signals.

Statistical Methods:

Counts were summarized as frequencies and relative frequencies. Distributions of counts were compared among groups with a chi-square test. Time-to-event data (survival and progression-free survival) were summarized by Kaplan-Meier estimation. Differences in time to event experiences between groups (i.e., those with deletion versus those without, those with fusion and those without) were compared with a Wilcoxon test. Univariable and multivariable analyses of time-to-event data were conducted using Cox proportional hazards modeling. The following variables were included in the modeling: age, gender, histologic type, mini-mental status exam (MMSE) status, 1p/19q deletion status, and CEP1/19p12 fusion status. The intent of the multivariable models was to ascertain whether the univariable association between deletion status and fusion and the time-to-event endpoints (survival and progression-free survival) remained after adjusting for known prognostic factors.

Example 2

Identifying a t(1;19)(q10p10) in an Oligodendroglioma

Figure 1:
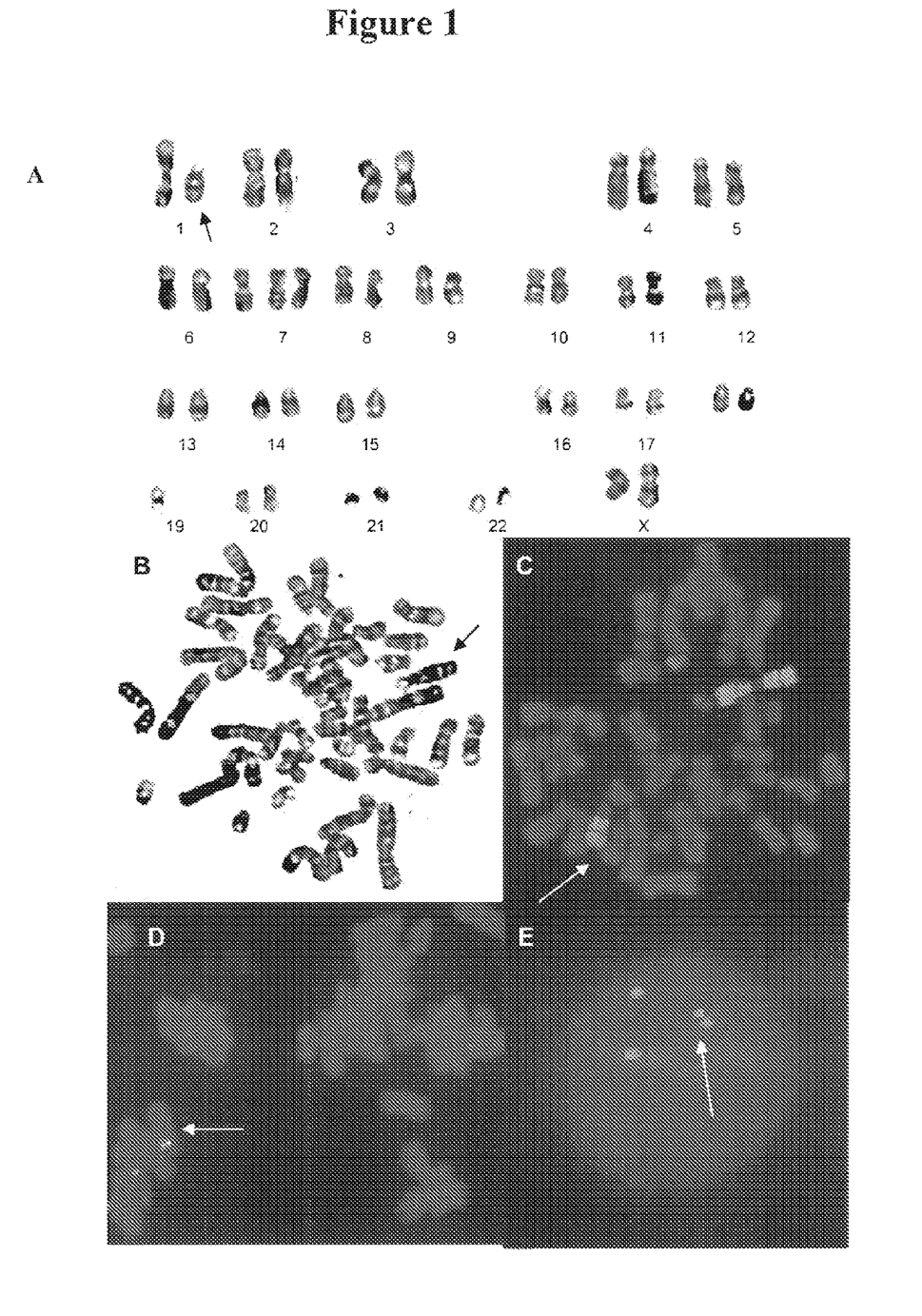

Using modifications of various stem cell media, a short-term culture and recovery of metaphases from a small number of oligodendrogliomas was performed. In one oligodendroglioma, an unbalanced 45,XX,der(1;19)(q10;p10) karyotype was observed in all abnormal metaphases (FIGS. 1A and B). Other nonclonal abnormalities, like an extra chromosome 7 (see FIG. 1A) were also observed in single metaphases. Initially, the translocation was verified in metaphases using WCP probes for chromosomes 1 and 19 (FIG. 1C). A BAC contig FISH probe set for proximal 19p12 in green was developed and combined with a CEP1 probe in orange. Using a single fusion strategy, this probe mixture was applied to metaphase cells and interphase nuclei from this glioma (FIGS. 1D and 1E). Fusion of the CEP1 and 19p12 probes was observed in all abnormal metaphases as well as 74% of interphase nuclei.

Example 3

Detecting t(1;19)(q10;p10) Using a CEP1/19p12 FISH Fusion Probe Set

The translocation probe set was applied to four non-tumor gliosis specimens, five oligodendroglioma paraffin specimens with (three) and without (two) 1p and 19q deletion, and a tissue microarray containing core biopsies from paraffin blocks from 16 oligodendrogliomas with (twelve) and without (four) 1p and 19q deletion. As described above, at least 60% of interphase nuclei were required to have co-localization of the CEP1 and 19 p12 signals for the tumor to be classified as having the t(1;19). Using this criterion, 17 (81%) oligodendrogliomas had evidence of fusion, and there was 90% concordance between co-deletion of 1p and 19q with fusion of the CEP1 and 19p12 probes on the tumor specimens (p<0.001). These included all 15 patients with co-deletion of 1p and 19q. In this group, the proportion of nuclei with fusion ranged from 62% to 98%. Two patients with fusion (respectively in 62 and 68% of nuclei) had no evidence of 1p and 19q co-deletion. Four patients had evidence of neither deletion nor fusion. The proportion of nuclei with fusion ranged from 4% to 35% in this group. The four non tumoral control specimens exhibited no evidence of the translocation while the proportion of nuclei having fusion ranged from 4% to 29%.

Example 4

1p and 19q Deletion as Well as CEP1 and 19p12 Fusion Predict Progression-free Survival and Overall Survival in Patients with Low-grade Gliomas Of 125 patients enrolled in NCCTG 94-72-53, paraffin blocks were available for 98 patients, and FISH studies for 1p/19q deletion were successful for 91 patients (93%). FISH studies for CEP1 and 19 p12 fusion were successful for 84 patients (86%). The reasons for unsuccessful FISH studies were block depletion (two patients—deletion, three patients—fusion), and hybridization failure (five patients—deletion, 11 patients—translocation). Table 1 compares characteristics of all eligible patients enrolled on the NCCTG trials to those of patients for whom FISH studies were successful. There were no significant differences in age, gender, MMSE and performance scores, treatment and histologic type among groups. Table 3 summarizes the 1p and 19q deletion and the CEP1/19p12 fusion results for each patient enrolled on 94-72-53.

TABLE 3

Individual 1p and 19q deletion and t(1;19) results for 98 patients enrolled on NCCTG trial 94-72-53.

| | Histologic type | 1p-(Y/N) | 19q-(Y/N) | CEP1/19p12 Fusion | Ploidy |
|---|---|---|---|---|---|
| 1 | astrocytoma | Y | F | N | A |
| 2 | astrocytoma | N | N | N | A |
| 3 | astrocytoma | N | N | N | A |
| 4 | astrocytoma | N | N | N | A |
| 5 | astrocytoma | F | F | N | A/D |
| 6 | astrocytoma | N | N | N | A/D |
| 7 | astrocytoma | N | N | N | A/D |
| 8 | astrocytoma | N | N | N | A/D |
| 9 | astrocytoma | N | N | N | D |
| 10 | astrocytoma | N | N | N | D |
| 11 | astrocytoma | N | Y | N | D |
| 12 | astrocytoma | N | N | N | D |
| 13 | astrocytoma | N | N | F | F |
| 14 | astrocytoma | N | N | F | F |
| 15 | astrocytoma | F | F | F | F |
| 16 | astrocytoma | N | N | F | F |
| 17 | astrocytoma | DB | DB | DB | DB |
| 18 | oligoastrocytoma | N | N | N | A |
| 19 | oligoastrocytoma | N | N | N | A |
| 20 | oligoastrocytoma | N | N | Y | A |
| 21 | oligoastrocytoma | N | Y | Y | A |
| 22 | oligoastrocytoma | N | N | N | A |
| 23 | oligoastrocytoma | N | N | Y | A |
| 24 | oligoastrocytoma | N | N | N | A |
| 25 | oligoastrocytoma | Y | Y | Y | A |
| 26 | oligoastrocytoma | Y | Y | Y | A |
| 27 | oligoastrocytoma | N | N | N | A |
| 28 | oligoastrocytoma | N | N | N | A |
| 29 | oligoastrocytoma | N | N | N | A |
| 30 | oligoastrocytoma | N | N | N | A/D |
| 31 | oligoastrocytoma | Y | Y | Y | A/D |
| 32 | oligoastrocytoma | Y | Y | Y | A/D |
| 33 | oligoastrocytoma | Y | Y | Y | A/D |
| 34 | oligoastrocytoma | N | N | N | A/D |
| 35 | oligoastrocytoma | Y | Y | Y | D |
| 36 | oligoastrocytoma | N | N | N | D |
| 37 | oligoastrocytoma | N | N | N | D |
| 38 | oligoastrocytoma | N | N | N | D |

TABLE 3-continued

Individual 1p and 19q deletion and t(1;19) results for 98 patients enrolled on NCCTG trial 94-72-53.

| | Histologic type | 1p-(Y/N) | 19q-(Y/N) | CEP1/19p12 Fusion | Ploidy |
|---|---|---|---|---|---|
| 39 | oligoastrocytoma | N | N | N | D |
| 40 | oligoastrocytoma | N | N | N | D |
| 41 | oligoastrocytoma | Y | Y | Y | D |
| 42 | oligoastrocytoma | Y | Y | Y | D |
| 43 | oligoastrocytoma | N | Y | N | D |
| 44 | oligoastrocytoma | N | N | Y | D |
| 45 | oligoastrocytoma | Y | Y | Y | D |
| 46 | oligoastrocytoma | Y | Y | Y | D |
| 47 | oligoastrocytoma | N | N | N | D |
| 48 | oligoastrocytoma | N | N | F | F |
| 49 | oligodendroglioma | N | N | N | A |
| 50 | oligodendroglioma | N | Y | N | A |
| 51 | oligodendroglioma | N | Y | N | A |
| 52 | oligodendroglioma | Y | Y | Y | A |
| 53 | oligodendroglioma | N | N | N | A |
| 54 | oligodendroglioma | N | N | Y | A |
| 55 | oligodendroglioma | N | N | N | A |
| 56 | oligodendroglioma | N | N | N | A |
| 57 | oligodendroglioma | Y | Y | Y | A/D |
| 58 | oligodendroglioma | N | N | Y | A/D |
| 59 | oligodendroglioma | Y | Y | Y | A/D |
| 60 | oligodendroglioma | Y | Y | Y | A/D |
| 61 | oligodendroglioma | Y | Y | Y | A/D |
| 62 | oligodendroglioma | N | N | N | A/D |
| 63 | oligodendroglioma | N | N | N | D |
| 64 | oligodendroglioma | Y | Y | Y | D |
| 65 | oligodendroglioma | Y | Y | Y | D |
| 66 | oligodendroglioma | N | N | N | D |
| 67 | oligodendroglioma | Y | Y | N | D |
| 68 | oligodendroglioma | Y | Y | N | D |
| 69 | oligodendroglioma | Y | Y | N | D |
| 70 | oligodendroglioma | Y | Y | Y | D |
| 71 | oligodendroglioma | N | N | N | D |
| 72 | oligodendroglioma | N | N | N | D |
| 73 | oligodendroglioma | Y | Y | Y | D |
| 74 | oligodendroglioma | Y | Y | Y | D |
| 75 | oligodendroglioma | F | F | Y | D |
| 76 | oligodendroglioma | N | N | N | D |
| 77 | oligodendroglioma | Y | Y | Y | D |
| 78 | oligodendroglioma | Y | Y | Y | D |
| 79 | oligodendroglioma | Y | Y | Y | D |
| 80 | oligodendroglioma | Y | Y | Y | D |
| 81 | oligodendroglioma | Y | Y | Y | D |
| 82 | oligodendroglioma | Y | Y | Y | D |
| 83 | oligodendroglioma | N | N | N | D |
| 84 | oligodendroglioma | Y | Y | Y | D |
| 85 | oligodendroglioma | Y | Y | Y | D |
| 86 | oligodendroglioma | Y | Y | Y | D |
| 87 | oligodendroglioma | N | Y | N | D |
| 88 | oligodendroglioma | N | N | N | D |
| 89 | oligodendroglioma | N | N | N | D |
| 90 | oligodendroglioma | Y | Y | Y | D |
| 91 | oligodendroglioma | F | F | F | F |
| 92 | oligodendroglioma | Y | Y | F | F |
| 93 | oligodendroglioma | Y | Y | F | F |
| 94 | oligodendroglioma | N | N | F | F |
| 95 | oligodendroglioma | Y | Y | F | F |
| 96 | oligodendroglioma | N | N | F | F |
| 97 | oligodendroglioma | Y | Y | F | F |
| 98 | oligodendroglioma | DB | DB | DB | DB |

Abbreviations:
Y = Yes;
N = No;
F = Failed Hybridization;
A = Aneuploid;
D = Diploid,
DB = Depleted Block The 1p and 19q deletion results were summarized (Table 4, part A). Of 91 patients with low grade glioma, 37 (41%) exhibited 1p and 19q co-deletion, six (6%) exhibited 19q deletion alone and 48 (53%) exhibited neither. In this group of patients, no case exhibited 1p deletion alone.

TABLE 4

Association of (A) Combined 1p and 19q Deletion and (B) t(1;19)(q10;p10) with Overall and Progression-free Survival in Patients with Low-grade Gliomas enrolled on NCCTG 94-72-53.

A. Overall and Progression Free Survival by 1p and 19q Deletion Status

| Histologic Type | Oligodendroglioma (N = 47) | Mixed Oligoastrocytoma (N = 31) | Astrocytoma (N = 13) | Total (N = 91) |
|---|---|---|---|---|
| PREVALENCE | | | | |
| 1p- and 19q- | 27 (57%) | 10 (32%) | 0 (0%) | 37 (41%) |
| Not 1p- and 19q- | 20 (43%) | 21 (68%) | 13 (100%) | 54 (59%) |
| OVERALL SURVIVAL | | | | |
| 5-year | | | | |
| 1p- and 19q- | 96% | 90% | — | 95% |
| Not 1p- and 19q- | 70% | 62% | 38% | 59% |
| Median, yrs. (CI) | | | | |
| 1p- and 19q- | 13.0 (11.2 to NR) | 11.0 (7.2 to NR) | — | 11.9 (10.4 to NR) |
| Not 1p- and 19q- | 10.8 (5.0 to 12.7) | 8.3 (3.9 to 13.0) | 3.1 (2.2 to NR) | 8.1 (4.1 to 11.2) |
| p-value* | 0.06 | 0.34 | — | 0.004 |
| PROGRESSION-FREE SURVIVAL | | | | |
| 5-year | | | | |
| 1p- and 19q- | 85% | 80% | — | 84% |
| Not 1p- and 19q- | 70% | 48% | 15% | 48% |
| Median, yrs. (CI) | | | | |
| 1p- and 19q- | 8.2 (5.5 to 11.1) | 8.1 (5.2 to 13.3) | — | 8.2 (5.8 to 10.4) |
| Not 1p- and 19q- | 7.0 (3.3 to 10.3) | 3.5 (2.7 to 6.2) | 1.4 (0.8 to 2.6) | 3.3 (2.5 to 6.2) |
| p-value* | 0.26 | 0.18 | — | 0.002 |

B. Overall and Progression Free Survival by CEP1/19p12 Fusion Status

| Histologic Type | Oligodendroglioma (N = 42) | Mixed Oligoastrocytoma (N = 30) | Astrocytoma (N = 12) | Total (N = 84) |
|---|---|---|---|---|
| PREVALENCE | | | | |
| CEP1/19p12 fusion | 23 (55%) | 14 (47%) | 0 (0%) | 37 (44%) |
| No CEP1/19p12 fusion | 19 (45%) | 16 (53%) | 12 (100%) | 47 (56%) |
| OVERALL SURVIVAL | | | | |
| 5-year | | | | |
| CEP1/19p12 fusion | 96% | 93% | — | 95% |
| No CEP1/19p12 fusion | 68% | 50% | 58% | 60% |
| Median, yrs. (CI) | | | | |
| CEP1/19p12 fusion | 13.0 (11.2 to NR) | 10.4 (7.3 to NR) | — | 11.9 (10.4 to NR) |
| No CEP1/19p12 fusion | 9.1 (5.0 to 12.7) | 6.4 (3.3 to 13.0) | 6.0 (3.1 to NR) | 8.1 (4.1 to 12.3) |
| p-value* | 0.01 | 0.17 | — | 0.003 |
| PROGRESSION-FREE SURVIVAL | | | | |
| 5-year | | | | |
| CEP1/19p12 fusion | 83% | 71% | — | 78% |
| No CEP1/19p12 fusion | 63% | 50% | 33% | 51% |

TABLE 4-continued

Association of (A) Combined 1p and 19q Deletion and (B) t(1;19)(q10;p10)
with Overall and Progression-free Survival in Patients with Low-grade Gliomas enrolled
on NCCTG 94-72-53.

| Median, yrs. (CI) | | | | |
|---|---|---|---|---|
| CEP1/19p12 fusion | 8.2 (5.5 to 10.3) | 7.2 (2.7 to 13.3) | — | 8.1 (6.2 to 10.3) |
| No CEP1/19p12 fusion | 5.6 (2.4 to 8.1) | 3.3 (1.7 to 11.0) | 1.6 (1.2 to 6.4) | 3.3 (2.4 to 5.8) |
| p-value* | 0.06 | 0.35 | — | 0.006 |

NR = not reached;
*Wilcoxon test

The prevalence of combined 1p and 19q deletion was 57% among 47 oligodendrogliomas, 32% among 31 mixed oligoastrocytomas, and 0% among 13 astrocytomas. The prevalence of combined 1p and 19q deletion was significantly different between all three histologic groups (p<0.001, chi square test).

Patients with 1p and 19q deletion had a median overall survival (OS) time of 11.9 years and a 5-year OS rate of 95% versus 8.1 years and 59%, respectively, for those without deletion (Wilcoxon p-value=0.004). The median progression free survival (PFS) time and 5-year PFS rate for patients with 1p and 19q deletion was 8.2 years and 84% versus 3.3 years and 48%, respectively, for those without deletion (Wilcoxon p-value=0.002).

In oligodendroglioma patients, median OS time and 5-year OS rate were 13 years and 96%, respectively, in patients with 1p and 19q co-deleted tumors versus 10.8 years and 70% in those without deletion (Wilcoxon p-value=0.06). Median PFS time and 5-year PFS rate were 8.2 years and 85%, respectively, in patients with 1p and 19q co-deleted tumors versus 7.0 years and 70% in those without deletion (Wilcoxon p-value=0.26).

An analysis of the combined set of 78 oligodendrogliomas and mixed oligoastrocytomas was performed. Patients with oligodendrogliomas or mixed oligoastrocytomas with 1p and 19q deletion had a median OS time of 11.9 years and a 5-year OS rate of 95%, versus 10.3 years and 66%, respectively, for those without deletion (Wilcoxon p-value=0.02). The median PFS rate and 5-year PFS rate for patients with 1p and 19q deletion was 8.2 years and 84% versus 5.6 and 59%, respectively, for those without deletion (Wilcoxon p-value=0.04).

The CEP1 and 19p12 fusion results were summarized (Table 4, part B). Of the 84 patients, 37 (44%) had CEP1/19p12 fusion, while 47 (56%) did not. The prevalence of fusion was 55% among 42 oligodendrogliomas, 47% among 30 mixed oligoastrocytomas, and 0% among 12 astrocytomas. The prevalence of fusion was significantly different between all three histologic groups (p<0.001, chi-square test).

1p and 19q deletion results were available for 81 of the 84 patients. The association of CEP1/19p12 fusion with chromosome 1p and 19q deletion data were summarized (Table 5). Briefly, of 33 gliomas with combined 1p and 19q deletion, 91% had CEP1/19p12 fusion. Of 48 gliomas without combined 1p and 19q deletion, 13% had CEP1/19p12 fusion. This difference inproportion was significant (p<0.001, chi-square test).

TABLE 5

Association of CEP1/19p12 fusion status with chromosome 1p and 19q deletion status among 81 low grade NCCTG gliomas.

| | 1p-/19q- | 19q- | Neither | Total |
|---|---|---|---|---|
| All Gliomas | | | | |
| CEP1/19p12 fusion | 30 | 1 | 5 | 36 |
| No CEP1/19p12 fusion | 3 | 5 | 37 | 45 |
| Oligodendrogliomas | | | | |
| CEP1/19p12 fusion | 20 | 0 | 2 | 22 |
| No CEP1/19p12 fusion | 3 | 3 | 13 | 19 |
| Mixed Oligoastrocytomas | | | | |
| CEP1/19p12 fusion | 10 | 1 | 3 | 14 |
| No CEP1/19p12 fusion | 0 | 1 | 15 | 16 |
| Astrocytomas | | | | |
| CEP1/19p12 fusion | 0 | 0 | 0 | 0 |
| No CEP1/19p12 fusion | 0 | 1 | 9 | 10 |

Figure 2:
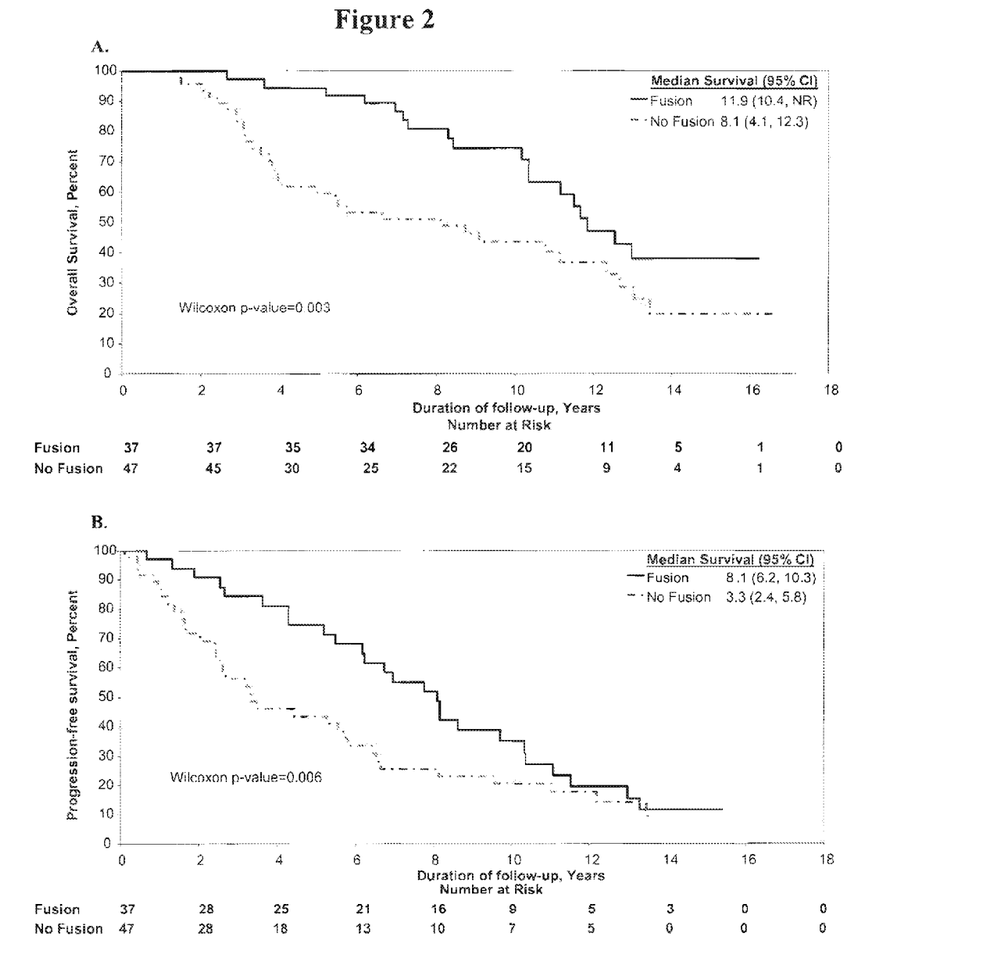
FIG. 2 is a series of survival curves for glioma patients with and without t(1;19)(q10;p10). A) Kaplan Meier curve for overall survival for patients with grade II gliomas with and without CEP1/19p12 fusion. B) Kaplan Meier curve for progression free survival for patients with grade II gliomas with and without CEP1/19 p12 fusion. C) Kaplan Meier curve for overall survival for patients with oligodendroglioma with and without CEP1/19p12 fusion. D) Kaplan Meier curve for progression free survival for patients with oligodendroglioma with and without CEP1/19p12 fusion. E) Kaplan Meier curves of overall survival by treatment and CEP1/19p12 fusion status for 61 patients with grade II gliomas enrolled on NCCTG 86-72-51. F) Kaplan Meier curves of progression-free survival by treatment and CEP1/19p12 fusion status for 61 patients with grade II gliomas enrolled on NCCTG 86-72-51.

Kaplan Meier survival curves were generated for median OS and PFS time for patients with grade II gliomas with and without CEP1/19p12 fusion (FIGS. 2A and 2B). Patients with fusion had a median OS time of 11.9 years and 5-year OS rate of 95% versus 8.1 years and 60%, respectively, for those without fusion (Wilcoxon p-value=0.003). The median PFS time and 5-year PFS rate for patients with fusion was 8.1 years and 78% versus 3.3 years and 51%, respectively, for those without the translocation (Wilcoxon p-value=0.006).

Kaplan Meier survival curves were generated for median OS and PFS time for patients with grade 11 oligodendrogliomas with and without CEP1/19p12 fusion (FIGS. 2C and 2D). Patients with oligodendrogliomas with fusion had a median OS time of 13.0 years and 5-year OS rate of 96% versus 9.1 years and 68%, respectively, for those without fusion (Wilcoxon p-value=0.01). The median PFS time and 5-year PFS rate for patients with fusion was 8.2 years and 83% versus 5.6 years and 63%, respectively, for those without the translocation (Wilcoxon p-value=0.06).

An analysis of the combined set of 72 oligodendrogliomas and mixed oligoastrocytomas was performed. Patients with oligodendrogliomas or mixed oligoastrocytomas with CEP1/19p12 fusion had a median OS time of 11.9 years and a 5-year OS rate of 95% versus 8.7 years and 60%, respectively, for those without fusion (Wilcoxon p-value=0.005). The median PFS time and 5-year PFS rate for patients with CEP1/19p12 fusion was 8.1 years and 78% versus 4.4 years and 57%, respectively for those without fusion (Wilcoxon p-value=0.05).

Example 5 t(1;19) or Combined 1p and 19q Deletion Status is Associated with Treatment Response One of the trial components of NCCTG 94-72-53, NCCTG 86-72-51, compared two doses of RT for low grade gliomas: 50.4Gy versus 64.8Gy (Shaw et al., *J. Clin. Oncol.*, 20(9): 2267-76 (2002)). The survival associations of combined 1p and 19q deletion or CEP1/19p12 fusion with these two radiation doses were summarized (Table 6). While no difference in OS between the two treatment arms was observed (Shaw et al., *J. Clin. Oncol.*, 20(9):2267-76 (2002))), there was evidence that patients without fusion had a significantly shorter OS when treated with higher doses of radiation (Table 6 and FIG. 2E). The hazard ratio for death after 64.8Gy of radiation, comparing patients without and with fusion, was 2.75 (95% CI: 1.14 to 6.65; likelihood ratio p-value=0.03; median OS 11.6 versus 5.0 years). Conversely, there was no significant difference in OS whether the patients with fusion received either a lower or higher dose of radiation (Table 6 and FIG. 2E). The hazard ratio for death after 64.8Gy versus 50.4Gy of radiation for patients with fusion was 1.59 (95% CI: 0.57 to 4.42; likelihood ratio p-value=0.37; median OS 11.6 versus not reached years). Similar results were observed for the association of PFS after RT with fusion status (Table 6 and FIG. 2F), and associations of OS and PFS after radiation therapy with combined 1p and 19q deletion status (Table 6).

TABLE 6

Association of (A) combined 1p and 19q deletion and (B) t(1;19)(q10;p10) with overall and progression-free survival by treatment arm in patients with low-grade glioma enrolled on NCCTG 94-72-53.

A. Overall and Progression Free Survival by Treatment Arm by 1p and 19q Deletion Status

| Treatment | 50.4 Gy 86-72-51 Arm A (N = 38) | 64.8 Gy 86-72-51 Arm B (N = 30) | 54.0 Gy/PCV 93-72-02 (N = 22) |
|---|---|---|---|
| OVERALL SURVIVAL | | | |
| 5-year | | | |
| 1p- and 19q- | 93% | 93% | 100% |
| Not 1p- and 19q- | 63% | 44% | 69% |
| Median, yrs. (CI) | | | |
| 1p- and 19q- | 13.4 (6.1, NR) | 11.6 (8.4 to 12.6) | 9.7 (9.1, 10.4) |
| Not 1p- and 19q- | 8.2 (3.9, 12.7) | 4.5 (3.7, 11.1) | 10.3 (3.3, NR) |
| p-value* | 0.09 | 0.02 | 0.12 |
| PROGESSION-FREE SURVIVAL | | | |
| 5-year | | | |
| 1p- and 19q- | 71% | 93% | 89% |
| Not 1p- and 19q- | 54% | 25% | 62% |
| Median, yrs. (CI) | | | |
| 1p- and 19q- | 7.3 (4.3, 13.0) | 8.2 (5.5, 11.5) | 8.6 (4.4, 10.4) |
| Not 1p- and 19q- | 5.7 (2.6, 7.2)) | 2.2 (0.8, 2.5) | 3.3 (1.1, 6.7) |
| p-value* | 0.34 | 0.002 | 0.08 |

B. Overall and Progression Free Survival by Treatment Arm by CEP1/19p12 Fusion Status

| Treatment | 50.4 Gy 86-72-51 Arm A (N = 34) | 64.8 Gy 86-72-51 Arm B (N = 27) | 54.0 Gy/PCV 93-72-02 (N = 22) |
|---|---|---|---|
| OVERALL SURVIVAL | | | |
| 5-year | | | |
| CEP1/19p12 fusion | 92% | 93% | 100% |
| No CEP1/19p12 fusion | 57% | 46% | 75% |
| Median, yrs. (CI) | | | |
| CEP1/19p12 fusion | NR (7.0, NR) | 11.6 (8.4, 12.6) | 10.4 (10.3, 10.4) |
| No CEP1/19p12 fusion | 8.1 (3.1, 12.7) | 5.0 (3.7, 6.6) | NR (9.1, NR) |
| p-value* | 0.07 | 0.004 | 0.10 |
| PROGRESSION-FREE SURVIVAL | | | |
| 5-year | | | |
| CEP1/19p12 fusion | 62% | 86% | 90% |
| No CEP1/19p12 fusion | 52% | 31% | 67% |
| Median, yrs. (CI) | | | |
| CEP1/19p12 fusion | 6.7 (4.3, 9.7) | 8.2 (5.5, 11.5) | 9.5 (2.7, 10.4) |
| No CEP1/19p12 fusion | 5.6 (2.5, 8.1) | 2.4 (0.8, 5.3) | 3.3 (1.1, 6.7) |
| p-value* | 0.43 | 0.003 | 0.09 |

NR = not reached;
*Wilcoxon test

The second trial component of NCCTG 94-72-53, the phase II trial 93-72-02, evaluated 6 cycles of PCV chemotherapy followed by 54.0Gy RT (Buckner et al., *J. Clin. Onco.*, 21(2):251-5 (2002)). The survival associations of combined 1p and 19q deletion or CEP1/19p12 fusion with this therapeutic approach were summarized (Table 6). There was a trend for patients without fusion to have a shorter PFS compared to patients with fusion. The hazard ratio for progression after 54.0Gy comparing patients without and with fusion was 7.39 (95% CI: 0.84 to 65.03; likelihood ratio p-value=0.03; median PFS 3.3 versus 9.5 years). Similar trends were observed for the association of OS after RT and PCV with fusion status and for the associations of OS and PFS after RT and PCV with combined 1p and 19q deletion (Table 6), but the p-values were not significant.

Example 6

Multivariable Modeling to Assess Associations with Patient Survival

Multivariable modeling was performed to assess whether the tumor deletion and fusion status remained associated with survival among the patients enrolled on 94-72-53 after adjusting for known prognostic factors. The univariable and multivariable Cox modeling results were summarized (Table 7). Briefly, using multivariable modeling, the hazard ratios for 1p and 19q deletion status did not change considerably from those in the univariable model, indicating that the association still remained after adjustment. However, the p-values did not achieve significance at the 0.05 level, likely due to the number of variables in the model and the relatively small sample size. The hazard ratios indicated a stronger association between CEP1/19p12 fusion status and OS than the deletion status. Although the p-values were not significant at 0.05, they do reveal evidence of an independent association between fusion status and OS in the whole cohort of low-grade gliomas and in the subset of mixed oligoastrocytomas plus oligodendrogliomas (p=0.10 and 0.08, respectively).

TABLE 7

Univariable and multivariable association of deletion status and fusion status with low grade glioma overall survival in NCCTG trial 94-72-53.

| | Univariable Model | | Multivariable Model* | |
|---|---|---|---|---|
| Variable | HR (95% CI) | p-value | HR (95% CI) | p-value |
| All low grade glioma cases (N = 91 for deletion; N = 84 for fusion) | | | | |
| Deletion status | | 0.03 | | 0.24 |
| 1p- and 19q- | 0.54 (0.31-0.93) | | 0.68 (0.36-1.29) | |
| Not 1p- and 19q- | 1.00 (ref) | | 1.00 (ref) | |
| CEP1/19p12 fusion status | | 0.02 | | 0.10 |
| CEP1/19p12 fusion | 0.50 (0.28-0.89) | | 0.58 (0.30-1.10) | |
| No CEP1/19p12 fusion | 1.00 (ref) | | 1.00 (ref) | |
| Mixed oligoastrocytoma and oligodendroglioma cases (N = 78 for deletion; N = 72 for fusion) | | | | |
| Deletion status | | 0.04 | | 0.19 |
| 1p- and 19q- | 0.55 (0.31-0.98) | | 0.65 (0.34-1.23) | |
| Not 1p- and 19q- | 1.00 (ref) | | 1.00 (ref) | |
| CEP1/19p12 fusion status | | 0.01 | | 0.08 |
| CEP1/19p12 fusion | 0.46 (0.25-0.56) | | 0.54 (0.28-1.06) | |
| No CEP1/19p12 fusion | 1.00 (ref) | | 1.00 (ref) | |
| Oligodendroglioma cases (N = 47 for deletion; N = 42 for fusion) | | | | |
| Deletion status | | 0.10 | | 0.31 |
| 1p- and 19q- | 0.51 (0.23-1.14) | | 0.63 (0.26-1.54) | |
| Not 1p- and 19q- | 1.00 (ref) | | 1.00 (ref) | |
| CEP1/19p12 fusion status | | 0.03 | | 0.14 |
| CEP1/19p12 fusion | 0.38 (0.16-0.90) | | 0.49 (0.19-1.27) | |
| No CEP1/19p12 fusion | 1.00 (ref) | | 1.00 (ref) | |

*Adjusting variables included in these models were age, gender, histologic type, and baseline Folstein mini-mental status exam (MMSE) score.

In summary, the results provided herein demonstrate that methods and materials for detecting a t(1;19)(q10;p10) (e.g., an unbalanced whole arm (centrosomal or pericentrosomal) translocation involving chromosomes 1 and 19) can be used to provide a prognosis for patients with low grade gliomas.

The FISH method used herein for detecting t(1;19) within interphase nuclei was somewhat different from prior interphase translocation strategies. The abnormal chromosome has the cytogenetic appearance of being the result of a whole arm (centrosomic or pericentrosomic) translocation. An initial probe choice to detect such alterations would be to use centromere-specific probes for chromosomes 1 and 19 (e.g. using a CEP1 and CEP19 in two different colors). However, there is significant sequence homology between the centromeres of chromosomes 1 and 19 (and 5) (Baldini et al., *Genomics*, 5(4):822-8 (1989)). Much of 19p12 and the entire 19cen (including the alpha satellite region) band is homologous to both 5cen and 1cen. As described herein, a FISH probe set was developed for proximal 19p12, using BACs that mapped close to the 19 centromere, but which lacked cross-hybridization with other genomic sequences; including chromosomes 1 and 5. Given the hypothesized size of most human centromeres, the CEP1 probe and the 19p12 probe set would be separated by at least 4.0 Mb (and at most 6.5 Mb) by the translocation. Given this distance, the expectation was not to observe actual fusion of the red and green signals (e.g., a merged yellow signal) within interphase nuclei that contained the translocation. Thus, the criteria for signal fusion was set to require that at least one red and one green signal to be within two signal diameters of each other. The resulting potential co-localization volume was large enough to result in random fusion events. The rate of random fusion was also increased by tumor aneuploidy and polyploidy. For example, trisomy 19 is a common alteration in glioblastomas. The final criteria for fusion, which minimized the false-positive and false-negative rate, required at least 60% of nuclei demonstrate co-localization of the red and green signals.

The strong homology of the chromosome 1 and 19 centromeric regions suggest a mechanism—centromeric or pericentromeric fusion—for the translocation. Since t(1;19) appears to be relatively specific for gliomas, and especially oligodendrogliomas, it is reasonable to speculate that regions of chromosomes 1 and 19 are co-localized, within early or more mature glial precursor cells and/or within mature oligodendroglial cells. Seven gliomas (two retrospective and five NCCTG tumors) were observed with evidence of fusion, but without deletion. While the discordant cases could be measurement errors, these gliomas may be evidence that co-localization precedes translocation or deletion.

As described herein, using prospectively-collected patients enrolled on cooperative group trials, combined deletion of 1p and 19q is confirmed to be associated with significantly prolonged OS and PFS in patients with low-grade oligodendrogliomas. In addition, patients with combined deletions may respond to lower doses of radiation, or higher doses of radiation may result in significant toxicity, especially in patients with combined deletion.

The results provided herein also demonstrate that the t(1; 19) that underlies the majority of the combined deletions is also associated with a prolonged overall and progression-free survival and response to radiation (as measured by survival). Multivariable analysis revealed that, in this group of patients, the t(1;19) is more strongly associated with OS than the combined deletion. While the multivariable results may be due to differences in FISH assay performance, they may also mean that the mechanism of combined deletion is of clinical and biologic relevance (e.g., that loss of 1p and 19q by translocation has different consequences compared to loss of 1p and 19q by other mechanisms). It is likely that the t(1;19) will also predict the prognosis of patients with anaplastic oligodendrogliomas and perhaps predict the initial response to chemotherapy in such patients.

The majority of combined 1p and 19q deletions associated with oligodendrogliomas were mediated by a single genetic event: a t(1;19)(q10;p10). The prevalence of this translocation in low-grade oligodendrogliomas was 44%. The results provided herein suggest that recurrent translocations are more common in solid tumors than previously appreciated. Finally, the results provided herein confirm that combined 1p and 19q deletions as well as the t(1;19) that mediates these translocations are independently associated with a significantly better prognosis in patients with low-grade gliomas, especially oligodendrogliomas.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining the prognosis of a human having low-grade glioma, said method comprising detecting a cancer cell from said human that contains a t(1;19)(q10; p10), and, determining that said human has a low-grade glioma that is less aggressive than a low-grade glioma having cancer cells lacking said t(1;19) (q10;p10).

2. The method of claim 1, wherein said detecting step comprises fluorescent in situ hybridization.

3. The method of claim 1, wherein said detecting step comprises fluorescent in situ hybridization with a CEP1 probe.

4. The method of claim 1, wherein said detecting step comprises fluorescent in situ hybridization with a 19p12 probe set.

5. A method of determining risk of cancer progression in a human having low-grade glioma, said method comprising detecting a cancer cell from said human that contains a t(1; 19)(q10;p10), and, if the determining that said human has an increased likelihood of progression-free survival as compared to a human having low-grade glioma having cancer cells lacking said t(1;19)(q10;p10).

6. The method of claim 5, wherein said detecting step comprises fluorescent in situ hybridization.

7. The method of claim 5, wherein said detecting step comprises fluorescent in situ hybridization with a CEP1 probe.

8. The method of claim 5, wherein said detecting step comprises fluorescent in situ hybridization with a 19p12 probe set.

9. A method of determining the prognosis of a human having low-grade glioma, wherein said method comprises:
    (a) detecting the presence of a t(1;19)(q10;p10) in a cancer cell from said human, and
    (b) classifying, based on said presence, said human as having a low-grade glioma that is less aggressive than a low-grade glioma having cancer cells lacking said t(1; 19) (q10;p10).

10. The method of claim 9, wherein said detecting step comprises fluorescent in situ hybridization.

11. The method of claim 9, wherein said detecting step comprises fluorescent in situ hybridization with a CEP1 probe.

12. The method of claim 9, wherein said detecting step comprises fluorescent in situ hybridization with a 19p12 probe set.

13. A method of determining risk of cancer progression in a human having low-grade glioma, wherein said method comprises:
    (a) detecting the presence of a t(1;19)(q10;p10) in a cancer cell from said human, and
    (b) classifying, based on said presence, said human has having an increased likelihood of progression-free survival as compared to a human having low-grade glioma having cancer cells lacking said t(1;19)(q10;p10).

14. The method of claim 13, wherein said detecting step comprises fluorescent in situ hybridization.

15. The method of claim 13, wherein said detecting step comprises fluorescent in situ hybridization with a CEP1 probe.

16. The method of claim 13, wherein said detecting step comprises fluorescent in situ hybridization with a 19p12 probe set.

* * * * *

UNITED STATES PATENT AND TRADEMARK OFFICE
CERTIFICATE OF CORRECTION

| | | |
|---|---|---|
| PATENT NO. | : 7,794,940 B2 | |
| APPLICATION NO. | : 11/744647 | |
| DATED | : September 14, 2010 | |
| INVENTOR(S) | : Robert B. Jenkins | |

It is certified that error appears in the above-identified patent and that said Letters Patent is hereby corrected as shown below:

Column 22, line 7 (Claim 5), before "determining" please delete "if the."

Column 22, line 40 (Claim 13), please delete "has" and insert --as-- therefor.

Signed and Sealed this
Eighteenth Day of January, 2011

David J. Kappos
*Director of the United States Patent and Trademark Office*